(12) United States Patent
Picha et al.

(10) Patent No.: US 6,375,231 B1
(45) Date of Patent: Apr. 23, 2002

(54) ENTERAL FEEDING CLAMP

(75) Inventors: George J. Picha, Independence; Gary Austin, Euclid; Eric Lab, Akron, all of OH (US)

(73) Assignee: Applied Medical Technology, Inc., Cleveland, OH (US)

( * ) Notice: Subject to any disclaimer, the term of this patent is extended or adjusted under 35 U.S.C. 154(b) by 0 days.

(21) Appl. No.: 09/522,733

(22) Filed: Mar. 10, 2000

(51) Int. Cl.[7] ................................................ F16L 13/04
(52) U.S. Cl. ........................................ 285/114; 604/905
(58) Field of Search ................................ 285/114, 241, 285/242; 439/369, 371; 24/336, 339; 604/905

(56) References Cited

U.S. PATENT DOCUMENTS

| | | |
|---|---|---|
| 874,378 A | 12/1907 | Allen |
| 1,384,962 A | 7/1921 | Kuhne |
| 3,179,442 A | 4/1965 | Lofgren |
| 3,295,548 A | 1/1967 | Woods |
| 3,813,733 A * | 6/1974 | Flohr ...................... 285/114 X |
| 3,881,753 A * | 5/1975 | Bochory ................. 285/114 X |
| 4,037,599 A | 7/1977 | Raulerson |
| 4,183,603 A * | 1/1980 | Donarummo ............... 439/369 |
| 4,230,109 A | 10/1980 | Geiss |
| 4,473,369 A | 9/1984 | Lueders et al. |
| 4,641,646 A | 2/1987 | Schultz et al. |
| 4,723,948 A | 2/1988 | Clark et al. |
| 4,832,618 A * | 5/1989 | Gunderson .................. 439/369 |
| 4,834,706 A * | 5/1989 | Beck et al. ................. 604/905 |
| 5,037,405 A | 8/1991 | Crosby |
| 5,057,093 A | 10/1991 | Clegg et al. |
| 5,248,306 A | 9/1993 | Clark et al. |
| 5,259,843 A | 11/1993 | Watanabe et al. |
| 5,322,073 A | 6/1994 | Michels et al. |
| 5,395,352 A | 3/1995 | Penny |
| 5,405,170 A * | 4/1995 | Roulinson et al. ...... 285/114 X |
| 5,443,397 A * | 8/1995 | Carl ........................... 439/369 |
| 5,507,533 A | 4/1996 | Mumma |
| 5,531,695 A | 7/1996 | Swisher |
| 5,554,140 A | 9/1996 | Michels et al. |
| 5,771,914 A | 6/1998 | Ling et al. |
| 5,873,608 A | 2/1999 | Tharp et al. |
| 5,876,234 A * | 3/1999 | Hester ........................ 439/369 |
| 6,165,149 A * | 12/2000 | Utterberg et al. ........... 604/905 |

FOREIGN PATENT DOCUMENTS

| | | | | |
|---|---|---|---|---|
| DE | 675077 | * | 4/1939 | .................. 24/339 |

* cited by examiner

*Primary Examiner*—Lynne H. Browne
*Assistant Examiner*—Greg Binda
(74) *Attorney, Agent, or Firm*—Pearne & Gordon LLP

(57) ABSTRACT

An enteral feeding clamp that secures a feeding adapter in relative position to a feeding device. The clamp includes C-shaped members integrally connected by one or more elastic webs. It also includes an elongated elastic band corresponding to each C-shaped member. The band has proximal and distal ends, and is integrally connected to the corresponding C-shaped member at its proximal end. Each of the elongated elastic bands has an enlarged head integrally formed at its distal end. A groove and receptacle are provided on the outer surface of each of the C-shaped members wherein the elastic band can be extended around the feeding adapter or feeding device, be placed in the groove, and have the head placed in the receptacle to secure the clamp in position. A method of using the feeding clamp is also provided.

18 Claims, 5 Drawing Sheets

ENTERAL FEEDING CLAMP

The invention relates generally to medical clamping devices. More particularly, it relates to an enteral feeding clamp for retaining a feeding tube and feeding device in close proximity to one another.

BACKGROUND OF THE INVENTION

The process of feeding a patient by the use of an enteral feeding device and a feeding tube is well known in the art. Typically, a gastrostomy device is implanted in a patient's stomach wall. The gastrostomy device is then connected to a feeding device via a tube. This, in turn, is connected to a feeding tube, usually via a "Christmas tree" adapter. Nutritional fluids are then transported via the feeding tube, through the adapter and feeding device and into the patient's stomach.

One of the common problems associated with this process is that the feeding tube and adapter may accidentally become disengaged from the feeding adapter during the course of feeding, and thus, the flow of nutritional fluids to the patient is interrupted.

Several solutions to this problem have been proposed, such as the inventions disclosed in U.S. Pat. No. 5,057,093 to Clegg et al., U.S. Pat. Nos. 5,322,073 and 5,554,140, both to Michels et al. Those interlock devices are all integrally formed with the feeding devices. Further, the device disclosed in the Michels et al. references cannot be removed from around the feeding tube until the tube has first been disengaged from the feeding device.

Clamping devices are also disclosed in U.S. Pat. No. 4,230,109 to Geiss and U.S. Pat. No. 5,248,306 to Clark et al. However, neither of those clamps have means for securing the clamp to the feeding device, outside of the axial forces discussed in Clark, et al. Further, neither of those clamps are elastic, and thus, cannot be used with feeding devices of varying sizes.

Therefore, it is desirable to provide an independent enteral feeding clamp that can be used with different size and style feeding devices and adapters, and that can be easily connected to and removed from such devices.

SUMMARY OF THE INVENTION

The present invention provides for an improved clamping device for retaining a feeding tube and feeding device in an interlocked position relative to one another.

The clamp comprises two or more C-shaped members that are integrally connected by one or more elastic webs. The C-shaped members are placed around a feeding tube and a feeding device, respectively, and are held in relative position by the elastic webs, as well as the frictional forces between the C-shaped members and the feeding apparatuses.

The C-shaped members are secured to the respective feeding apparatuses by one or more elastic bands. The elastic bands are integrally connected to the C-shaped members at their proximal ends, and include enlarged heads at their distal ends.

The C-shaped members also include a groove and receptacle which are formed in the outer surface of the member. The groove and receptacle are sized to receive the elastic bands and their respective enlarged heads. The groove is also sized to be smaller than the outer diameter of the enlarged head.

The elastic bands substantially encircle the respective feeding apparatuses and are disposed in the groove, while the elongated head is placed in the receptacle. The band is kept in place by the frictional forces between the band and the groove, as well as the fact that the groove is smaller than the enlarged head, thus preventing the band from retracting to its natural position.

The clamp is integrally formed from an elastomeric material, preferably silicone.

BRIEF DESCRIPTION OF THE DRAWINGS

A fuller understanding of the invention may be had by referring to the following description and claims, taken in conjunction with the accompanying drawings, wherein:

DETAILED DESCRIPTION OF THE PREFERRED EMBODIMENTS

Figure 1:
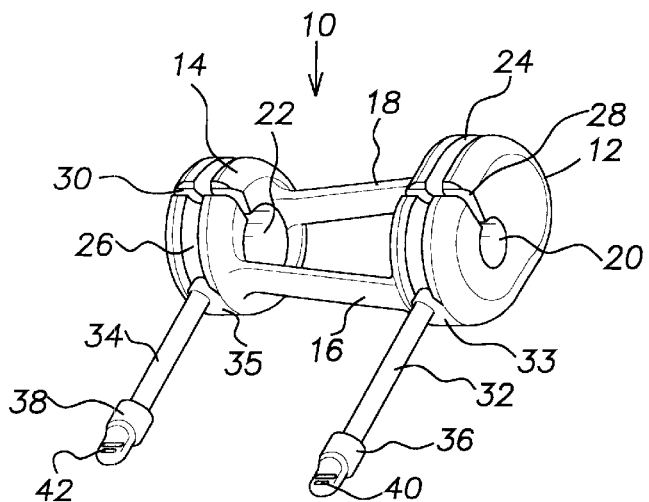
FIG. 1 is a perspective view of the preferred embodiment of an enteral feeding clamp in accordance with the present invention.
Figure 2:
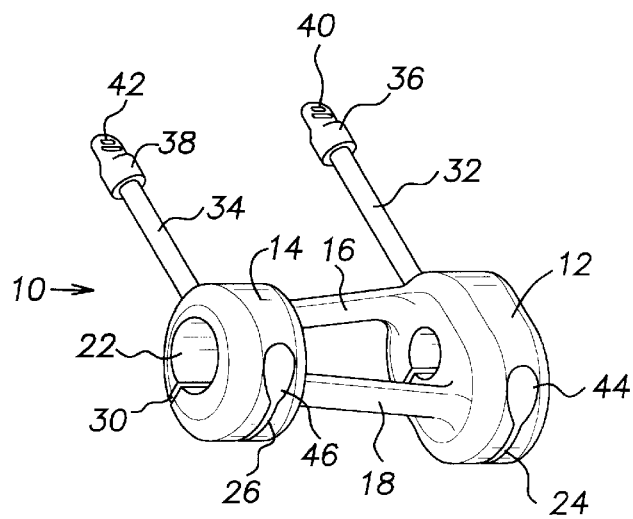
FIG. 2 is an alternate perspective view of the embodiment illustrated in FIG. 1.
Figure 3:
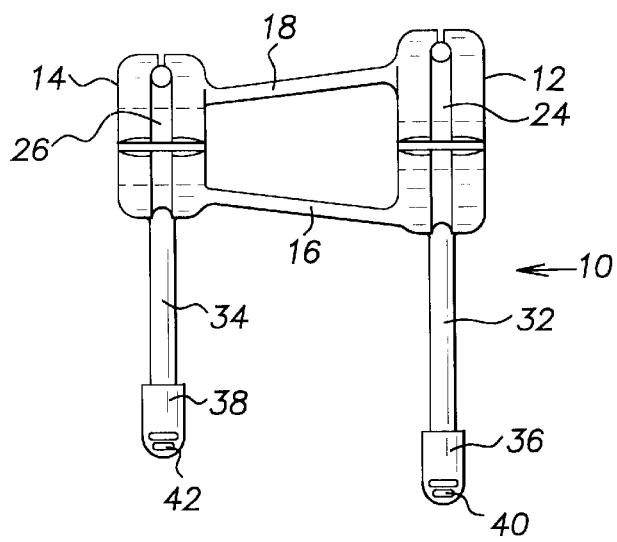
FIG. 3 is a top view of the embodiment illustrated in FIGS. 1–2.

With reference to FIGS. 1–3, the preferred embodiment of an enteral feeding clamp 10 is illustrated. The clamp is comprised of two or more C-shaped members 12 and 14. Each member is formed so as to have an aperture or bore 20 and 22, respectively, through the center of the member, as well as an opening slot or mouth 28 and 30, respectively, to allow the member to open up and wrap around a feeding tube or feeding device. Preferably, the bores, 20 and 22, are of different diameters to allow the clamp to be connected to feeding tubes and devices that are different sizes.

The C-shaped members 12 and 14 are held to each other by connecting means comprising a pair of elastic tethers or webs 16 and 18. The webs are integrally formed with the C-shaped members. The two webs preferably are diametrically opposite one another, to provide the most stability for the clamp. It can be easily seen that the elasticity of the webs will allow the clamp to be attached to feeding tubes and devices of varying sizes, and at different places on the same tube/device system.

The C-shaped members are held in position relative to the feeding tube/device system by securing means comprising elongated straps or bands 32 and 34, extending from and integrally formed with the C-shaped members, said bands having both proximal and distal ends. The bands are formed at their proximal ends 33 and 35 with the C-shaped members. The bands terminate in enlarged heads 36 and 38 at their distal ends. The enlarged heads preferably include raised notches 40 and 42 disposed thereon, which provide frictional means for gripping the enlarged heads.

The C-shaped members are formed so as to have outer surfaces wherein channels or grooves 24 and 26 are formed. The grooves originate at a position immediately adjacent to the proximal ends 33 and 35 of bands 32 and 34. The grooves extend along the outer surfaces of the C-shaped members, crossing through and essentially perpendicular to the mouths 28 and 30. The grooves terminate in receptacles 44 and 46. Grooves 24 and 26 are sized to be substantially as wide as the outer diameter of the elongated bands 32 and 34. In this manner, the bands may be placed inside the grooves, while the outer surfaces of the bands are in contact with the inner surfaces of the grooves. Thus, when a band is stretched around the outer surface of the C-shaped member and placed inside the groove, the frictional forces between the inner surface of the groove and the outer surface of the band help prevent the band from retracting back to its original position.

Figure 6:
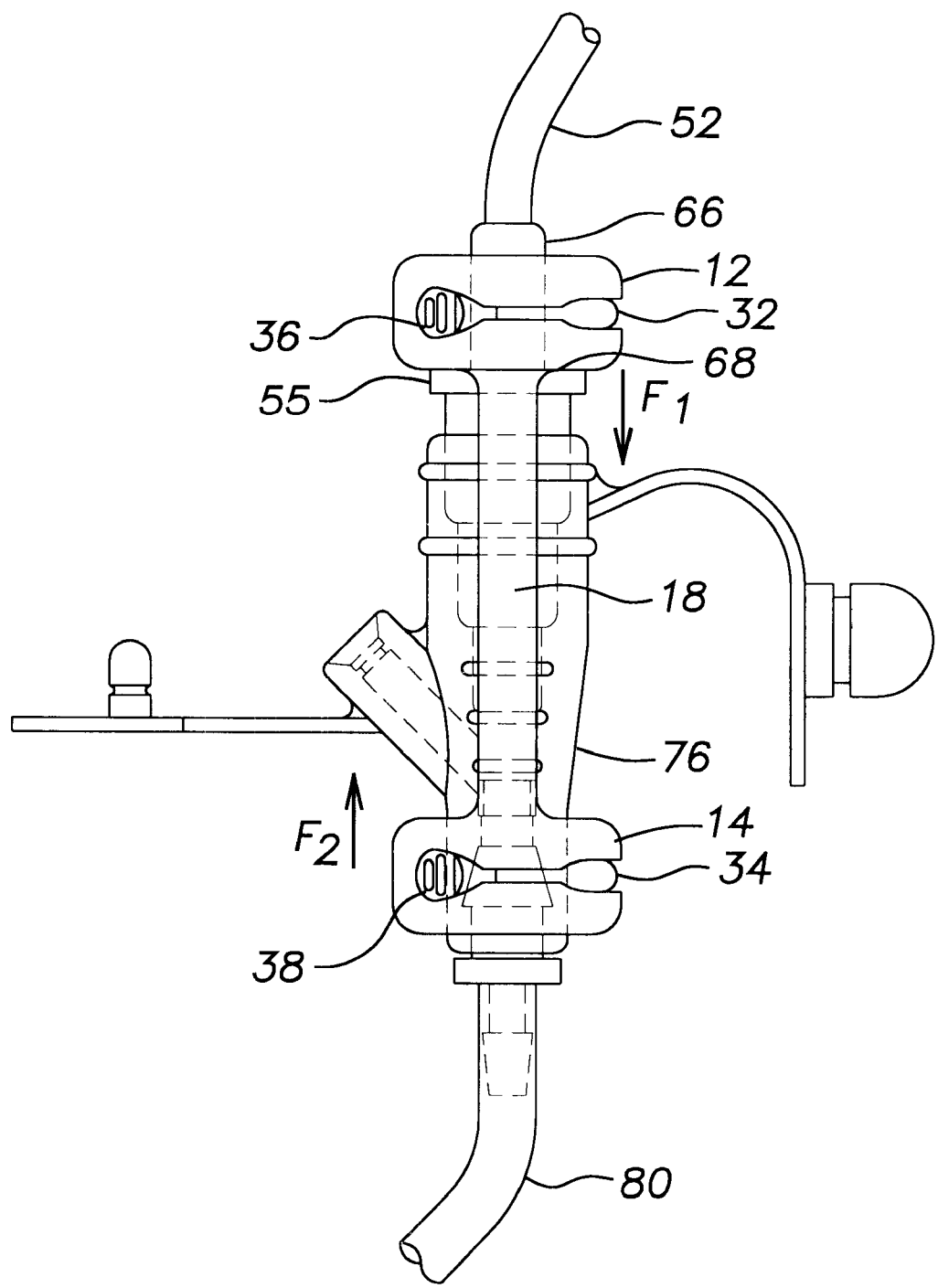
FIG. 6 is a side view similar to FIG. 5 showing the enteral feeding clamp fully attached to a feeding tube/device system.

The enlarged heads 36 and 38 are sized so as to be wider than grooves 24 and 26. Further, receptacles 44 and 46 (shown in FIG. 2) are sized so as to receive heads 36 and 38. Thus, when a band is placed in its corresponding groove, and the enlarged head placed in the receptacle as seen in FIG. 6, the head cannot move out of the receptacle and back through the groove because the head is wider than the groove. In this way, the head and groove also keep the band from retracting back to its original position.

Figure 7:
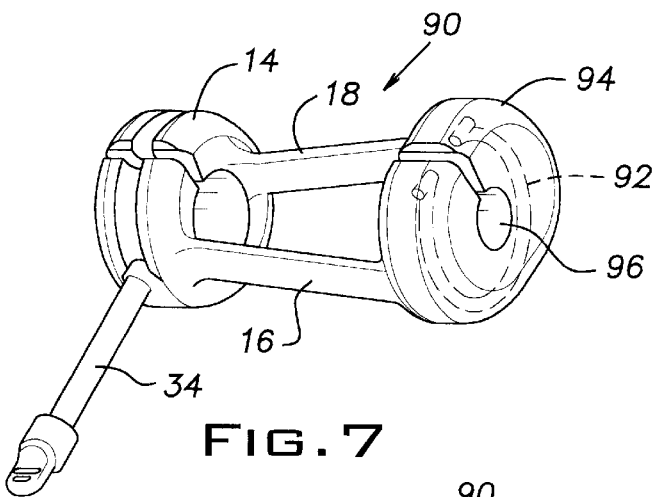
FIG. 7 is a perspective view of a second embodiment of an enteral feeding clamp in accordance with the present invention.
Figures 7A, 8:
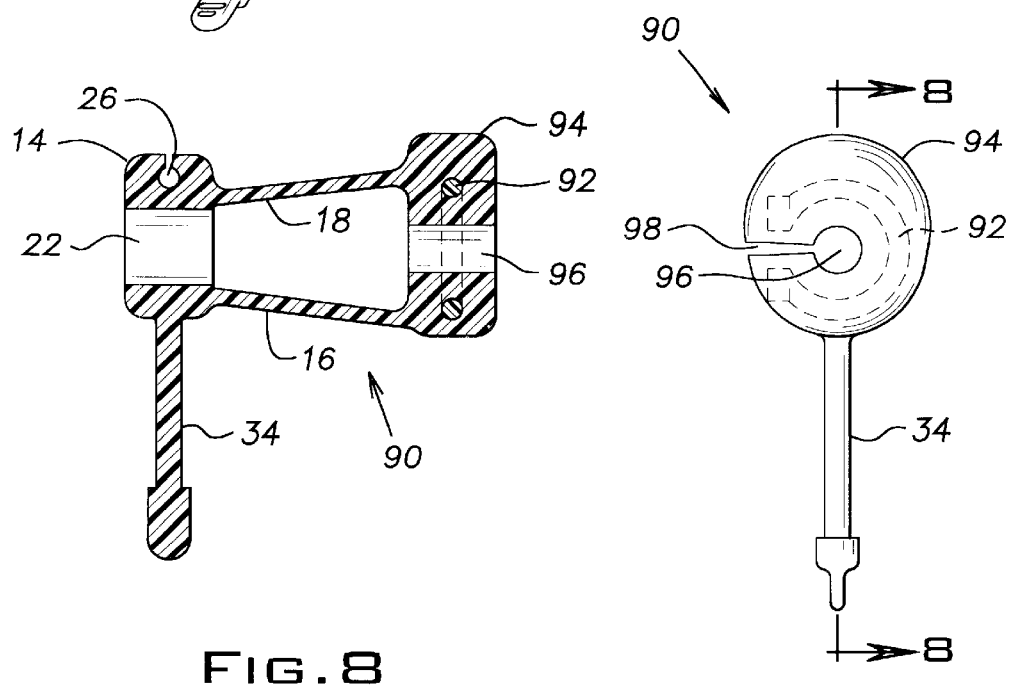
FIG. 7a is a side view of the clamp of FIG. 7.
FIG. 8 is a cut-away view of the clamp of FIG. 7a, taken along line 8—8.

A second embodiment of the feeding clamp is illustrated in FIGS. 7–8. In this embodiment, the securing means for C-shaped member 94 comprises a resilient plastic insert 92, formed inside of the member itself. Plastic insert 92 is slightly elastic, thus it still allows mouth 98 to open. However, the resiliency of plastic insert 92 limits the flexibility of C-shaped member 94, and in turn, the amount that mouth 98 can open. In that way, insert 92 reduces the chance that the feeding tube/device disposed within bore 96 can become dislodged. Furthermore, the resiliency causes C-shaped member 94 to retract to its original position, thus keeping the member closed around the feeding tube/device. In this embodiment, a resilient plastic insert can be used in more than one C-shaped member. If a resilient plastic insert is formed in a C-shaped member, it is not necessary to also have the elongated bands and corresponding grooves. Thus, all of the C-shaped members can have resilient plastic inserts, and no elongated bands and grooves.

Figure 9:
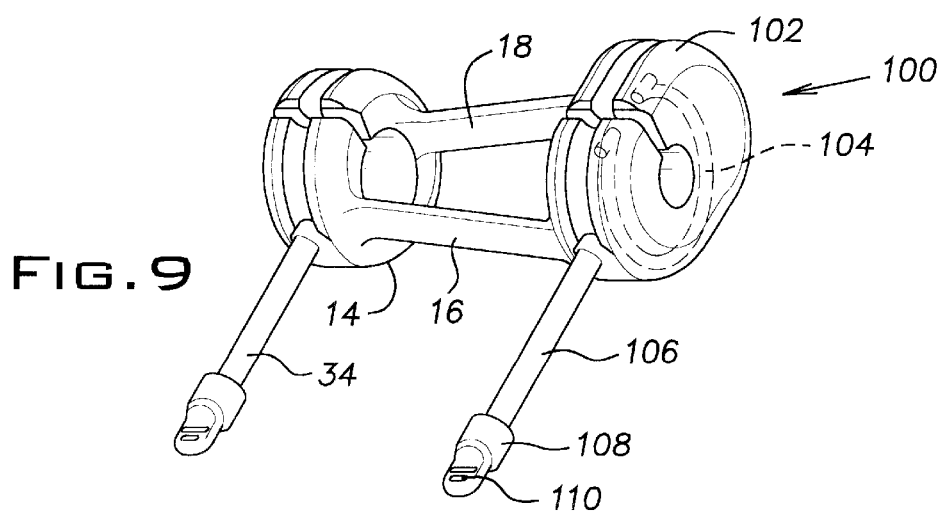
FIG. 9 is a perspective view of a third embodiment of an enteral feeding clamp in accordance with the present invention.

In a third embodiment shown in FIG. 9, the securing means comprises a combination of elastic band 106, enlarged head 108, groove 112, receptacle 114 (not shown) and resilient plastic insert 104. Here, the band 106 functions to secure the clamp 100 to the feeding device or tube, while the resilient plastic insert 104 provides additional security should the elastic band 106 manage to become dislodged from groove 112. In this embodiment, the securing means in the preferred embodiment is supplemented by a resilient plastic insert in all of the C-shaped members.

Figure 4:
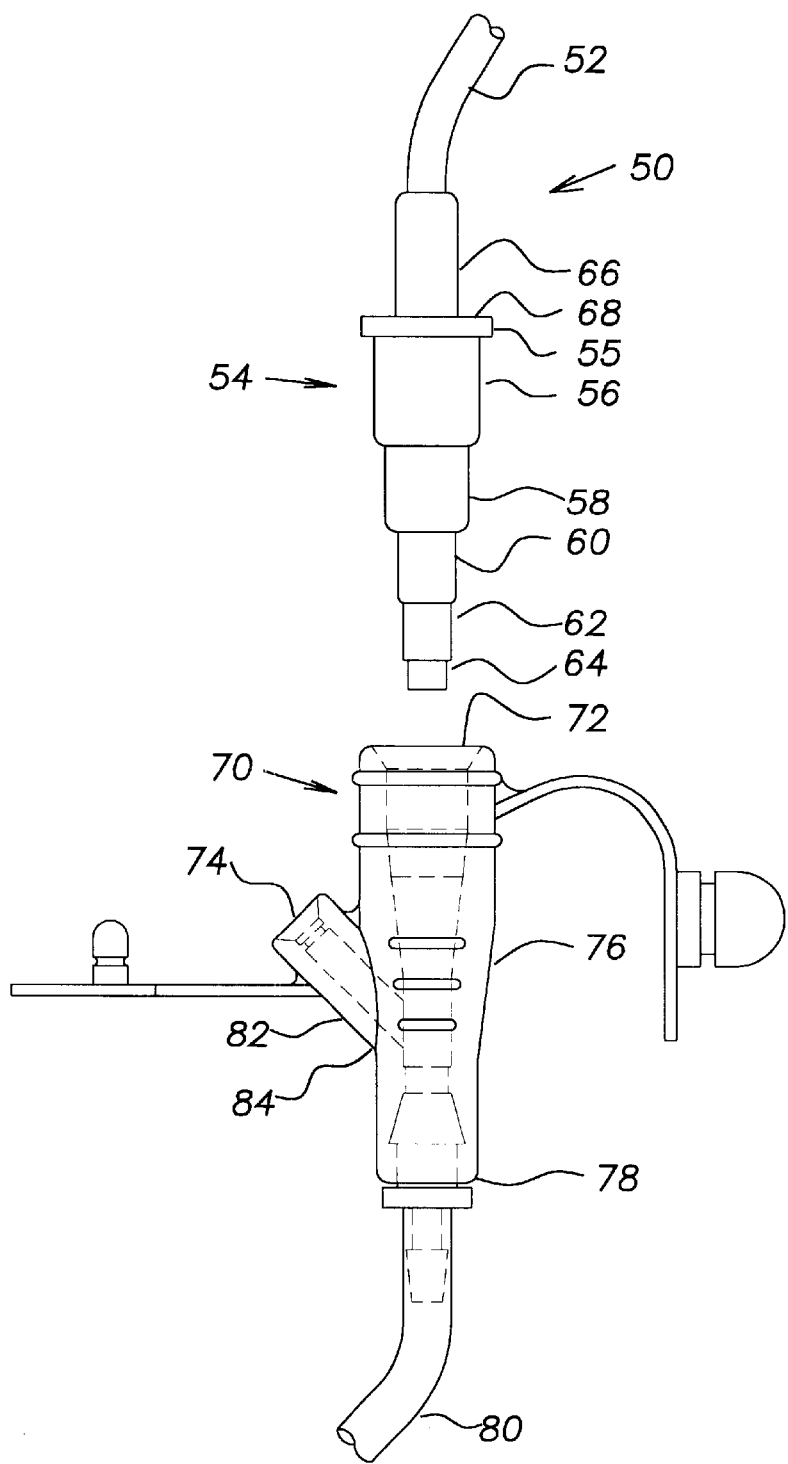
FIG. 4 is a diagrammatic view of a feeding device and a feeding adapter, the environment in which the feeding clamp will commonly be used.
Figure 5:
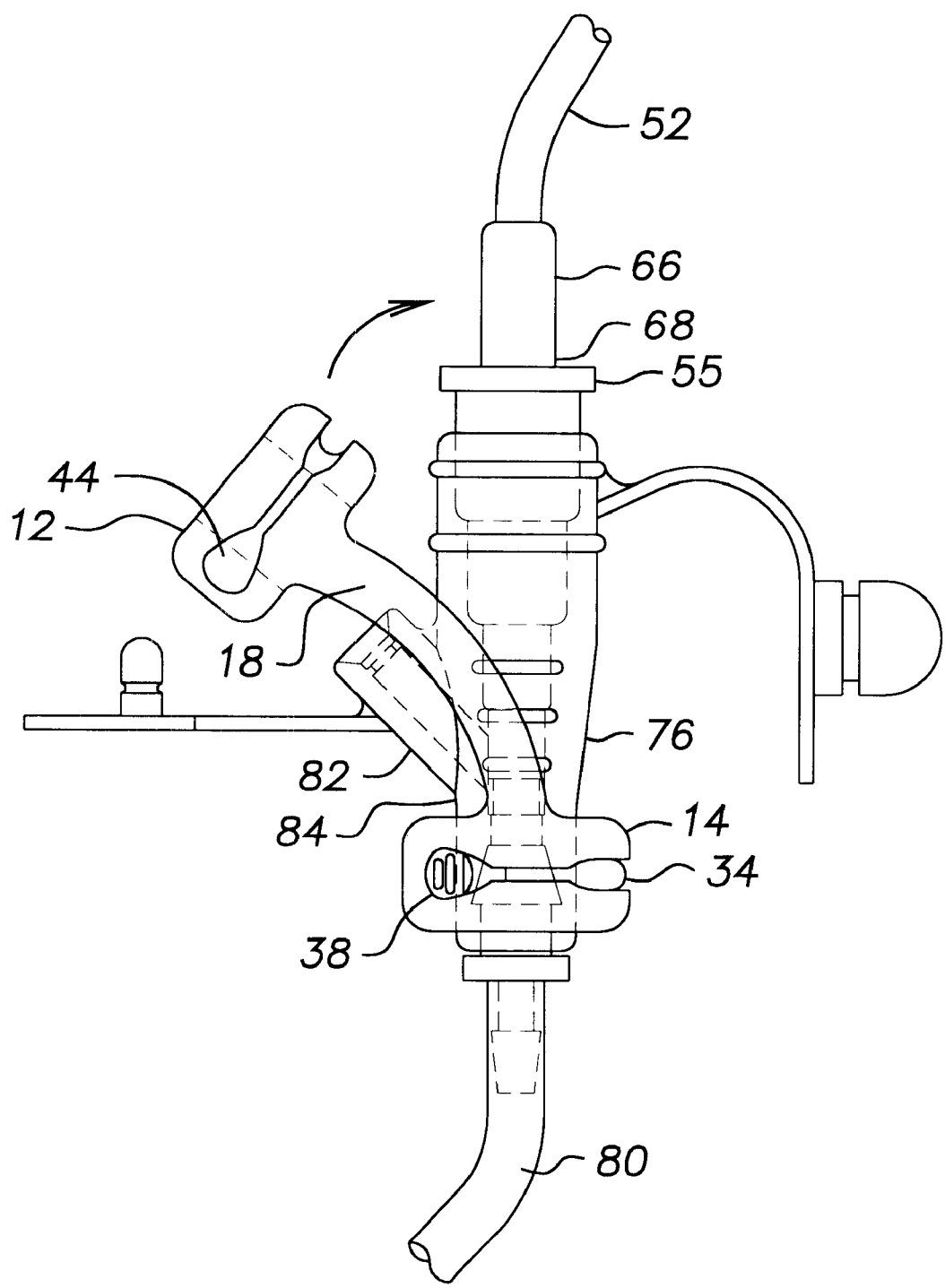
FIG. 5 is a side view of the preferred embodiment of an enteral feeding clamp partially attached to a feeding tube/device system.

With reference to FIGS. 4–6, a feeding tube/device assembly is shown in conjunction with the preferred embodiment of the enteral feeding clamp. FIG. 4 shows a typical feeding tube/device arrangement prior to assembly. Feeding tube 50 generally comprises a tube 52 which is connected to a feeding bag on one end by generally known means, and on its other end is connected to feeding adapter 54. Feeding adapter 54 is of a type generally known in the art, and will usually comprise a series of decreasing diameter cylindrical sections 55, 56, 58, 60, 62 and 64, with the section of smallest diameter being the first section inserted into feeding device 70. Feeding adapter 50 also comprises a cylindrical insertion port 66, integrally formed with and adjacent to the largest diameter cylindrical section 55. Insertion port 66 is sized to be slightly larger than, and thus receive, feeding tube 52. The insertion port and cylindrical section 55 form a lip 68, which may be utilized by feeding clamp 10 as will be described below.

Also illustrated in FIG. 4 is feeding device 70, which is preferably a Y-port or G-tube adapter as is known in the art. Feeding device 70 generally comprises a main port 72, and a secondary port 74. The main port 72 is sized so as to receive feeding adapter 54, as shown in FIG. 5. Feeding device 70 further comprises a main body 76, which is generally cylindrical in shape, but of slightly and gradually decreasing diameter from the main port to the end 78 which is connected to a tube 80 which leads to a patient's stomach. Main port 72 consists of an opening formed through the center of and axially aligned with main body 76. A secondary body 82, also of generally cylindrical shape and containing secondary port 74, but of smaller diameter than main body 76, is integrally formed with and protrudes at an angle from main body 76. The junction 84 between secondary body 82 and main body 76 may also be utilized by feeding clamp 10 as will be described below.

FIG. 5 shows feeding tube 50 and feeding device 70 in an interlocked position. In order to keep this system in a substantially interlocked position, feeding clamp 10, as shown in FIGS. 1–3, is used.

C-shaped member 14 is deformed in a manner effective to widen mouth 30 a sufficient distance to allow the section of main body 76 below junction 84 to be disposed in bore 22. C-shaped member 14 is then allowed to retract to its natural position, thus substantially closing around main body 76. In this position, the inside surface of C-shaped member 14 is in contact with the outer surface of main body 76. Thus, the frictional forces between the two surfaces help keep C-shaped member 14 from sliding along main body 76.

Elastic band 34 is extended to substantially encircle the outer surface of C-shaped member 14 such that band 34 is disposed in groove 26, and passing through the intersection between groove 26 and mouth 30. Enlarged head 42 is then placed inside receptacle 46. Band 34 cannot retract back to its relaxed position because enlarged head 42 is larger than groove 26. Band 34 and head 42 thus keep mouth 30 from opening sufficient to allow main body 76 to dislodge from bore 22. It can easily be seen that, because feeding clamp 10 is formed of an elastomeric material, C-shaped member 14 can stretch slightly, and therefore, the fit between bore 22 (when C-shaped member 14 is in its relaxed position) and main body 76 need not be exact. Thus, feeding clamp 10 can accommodate feeding devices of different body diameters.

In a similar manner, C-shaped member 12 is disposed around feeding tube 50, as illustrated in FIG. 6. Webs 16 and 18 are stretched until mouth 28 is in a position where it is clear of lip 68, and can open and envelop insertion port 66. C-shaped member 12 is then deformed in a manner effective to widen mouth 28 a to allow insertion port 66 to be disposed in bore 20. C-shaped member 12 is then allowed to retract to its natural position, thus substantially closing around insertion port 66. In this position, the inside surface of C-shaped member 12 is in contact with the outer surface of insertion port 66.

Elastic band 32 is extended to substantially encircle the outer surface of C-shaped member 12 such that band 32 is disposed in groove 24, and passing through and perpendicular to mouth 28. Enlarged head 40 is then placed inside receptacle 44. In this position, C-shaped member 12 is in contact with lip 68 in a manner sufficient to keep webs 16 and 18 from retracting to their natural positions, thus dislodging insertion port 66 from bore 20.

As discussed above, feeding clamp 10 is made of an elastomeric material, preferably silicone. As such, when webs 16 and 18 are in an elongated state, the material naturally tends to retract back to its original position. This tendency exerts equal, diametrically opposed forces on C-shaped members 12 and 14 in a plane substantially parallel to webs 16 and 18, as indicated in FIG. 6 by arrows F1 and F2. C-shaped members 12 and 14 are in contact with lip 68 and secondary port 82 at junction 84, respectively. Thus, the forces F1 and F2 are transferred to lip 68 and secondary port 82, in the same direction the forces are exerted on C-shaped members 12 and 14. If there is no secondary port 82 provided, or if C-shaped member 14 is connected below junction 84 so as not to be in contact with secondary port 82, then F2 is transferred to main body 76 by way of frictional forces. In this way, forces F1 and F2 act to pull feeding device 70 and feeding tube 50 towards each other, and therefore, keep the two apparatuses in a substantially interlocked position.

Of course, it should be apparent that the device need not be used only in conjunction with a feeding tube/device system. The clamp can be used to keep any two or more tubular devices, which have sections that will fit inside bores 20 and 22, in a relatively interlocked position.

It should be evident that this disclosure is by way of example, and that various changes may be made by adding, modifying or eliminating details without departing from the fair scope of the teaching contained in this disclosure. The invention is therefore not limited to the particular details of the disclosure except to the extent that the following claims are necessarily so limited.

What is claimed is:

1. A tube clamp for holding two interlocking tubular devices in position relative to each other, the interlocking tubular devices having a longitudinal extent, the tube clamp including:
    at least two elastic C-shaped members, the C-shaped members being spaced from each other along the longitudinal extent of the tubular devices, each C-shaped member defining a mouth at which the C-shaped member receives a respective one of the tubular devices and a bore at which the C-shaped member engages the respective tubular device;
    at least one elastic web coupling the C-shaped members to each other, each web being integrally formed with the two C-shaped members, each web being elastically deformable under applied force to increase distance between the C-shaped members and providing a pulling force to the C-shaped members along the longitudinal extent of the tubular devices; and
    at least one retainer component for holding a respective C-shaped member in engagement with the respective tubular device;
    wherein each retainer component including a band integrally formed with the respective C-shaped member, the band extending from the respective C-shaped member on a first side of the mouth of the respective C-shaped member, being extendable across the mouth from the first side to a second side of the mouth, and being securable at the second side.

2. A tube clamp as set forth in claim 1, wherein the entire clamp is integrally formed of an elastomeric material.

3. A tube clamp as set forth in claim 1, wherein the at least one elastic web includes at least two elastic webs, the elastic webs being diametrically opposed relative to each other.

4. A tube clamp as set forth in claim 1, wherein the at least one retainer component includes at least two retainer components.

5. A tube clamp as set forth in claim 1, including an additional retainer component, the additional retainer component for holding a respective C-shaped member in engagement with the respective tubular device, the entire tube clamp except for the additional retainer component being made of elastic material, the additional retainer component being made of material having lesser elasticity than the elastic material, and the additional retainer component being C-shaped and being located within the respective C-shaped member.

6. A tube clamp as set forth in claim 1, wherein the band has an enlarged head located on a distal end.

7. A tube clamp as set forth in claim 6, wherein the C-shaped member on the second side of the mouth has a groove, the band fitting into the groove, and the enlarged head holding the band in the groove.

8. A tube clamp as set forth in claim 7, wherein the groove has a first portion with a first width for receiving a portion of the band adjacent to the enlarged head, and a second portion with a second, greater width for receiving the enlarged head.

9. A tube clamp as set forth in claim 1, wherein the band is elastically deformable under applied force to increase length of the band and providing a pulling force across the mouth of the C-shaped member from the first side to a second.

10. A clamp for holding two interlocked tubular devices in position relative to each other, comprising two C-shaped members, each of said C-shaped members defining a bore and a mouth, and having an outer surface, two diametrically opposed elastic webs integrally formed between the C-shaped members, two elongated elastic bands having a proximal end and a distal end, each elastic band integrally formed with one of the C-shaped members at its proximal end, and including an enlarged head at its distal end, and a groove and receptacle formed in the outer surface of each of the C-shaped members such that the groove in each C-shaped member receives the elastic band integrally connected to that particular C-shaped member, and the receptacle receives the corresponding enlarged head.

11. A tube clamp for holding two interlocking tubular devices in position relative to each other, the interlocking tubular devices having a longitudinal extent, the tube clamp comprising:
    at least two elastic C-shaped members, the C-shaped members being spaced from each other along the longitudinal extent of the tubular devices, each C-shaped member defiling a mouth at which the C-shaped member receives a respective one of the tubular devices and a bore at which the C-shaped member engages the respective tabular device;
    at least one elastic web coupling the C-shaped members to each other, each web being integrally formed with the two C-shaped members, each web being elastically deformable under applied force to increase distance between the C-shaped members and providing a pulling force to the C-shaped members along the longitudinal extent of the tubular devices; and at least one retainer component for holding a respective C-shaped member in engagement with the respective tubular device;

wherein the entire tube clamp except for the retainer component being made of elastic material, the retainer component being made of material having lesser elasticity than the elastic material, and the retainer component being C-shaped and being located with the respective C-shaped member.

12. A tube clamp as set forth in claim 11, wherein the at least one elastic web includes at least two webs.

13. A tube clamp as set forth in claim 12, wherein the two webs are diametrically opposed from each other.

14. A tube clamp as set forth in claim 11, including an additional retainer component for holding a respective C-shaped member in engagement with a respective tubular device, the additional retainer component includes a band integrally formed with the respective C-shaped member and extending from the respective C-shaped member on a first side of the mouth, the band is extendable across the mouth from the first side to a second side of the mouth and is securable at the second side.

15. A tube clamp as set forth in claim 14, wherein the band has an enlarged head located on a distal end.

16. A tube clamp as set forth in claim 15, wherein the respective C-shaped member on the second side of the mouth bas a groove, the band fitting into the groove, and the enlarged head holding the band in the groove.

17. A tube clamp as set forth in claim 16, wherein the groove has a first portion with a first width for receiving a portion of the band adjacent to the enlarged head, and a second portion with a second, greater width for receiving the enlarged head.

18. A tube clamp as set forth in claim 14, wherein the band is elastically deformable under applied force to increase length of the band and providing a pulling force across the mouth of the respective C-shaped member from the first side to a second.

* * * * *

UNITED STATES PATENT AND TRADEMARK OFFICE
CERTIFICATE OF CORRECTION

PATENT NO. : 6,375,231 B1
DATED : April 23, 2002
INVENTOR(S) : George J. Picha, Gary Austin and Eric Lab It is certified that error appears in the above-identified patent and that said Letters Patent is hereby corrected as shown below:

<u>Column 6,</u>
Line 57, please delete "defiling", and insert therefor -- defining --.

<u>Column 8,</u>
Line 7, please delete "bas", and insert therefor -- has --.

Signed and Sealed this

Ninth Day of July, 2002

Attest:

JAMES E. ROGAN
Attesting Officer     Director of the United States Patent and Trademark Office